United States Patent [19]
Platt

[11] Patent Number: 5,891,861
[45] Date of Patent: *Apr. 6, 1999

[54] COMPOSITION AND METHOD FOR TREATING FUNGAL DISEASE IN ANIMALS

[76] Inventor: David Platt, One Kendall Sq. Bldg. 300, Cambridge, Mass. 02139-9645

[ * ] Notice: This patent issued on a continued prosecution application filed under 37 CFR 1.53(d), and is subject to the twenty year patent term provisions of 35 U.S.C. 154(a)(2).

[21] Appl. No.: 730,367

[22] Filed: Oct. 15, 1996

[51] Int. Cl.⁶ .......................... A61K 31/73; A61K 31/735
[52] U.S. Cl. .................................. 514/55; 514/54; 514/61; 514/62
[58] Field of Search .................................. 514/54, 55, 61, 514/62; 536/29.1

[56] References Cited

U.S. PATENT DOCUMENTS

| | | | |
|---|---|---|---|
| 4,159,932 | 7/1979 | Peniston et al. | 204/158 |
| 4,701,444 | 10/1987 | Segal et al. | 514/55 |
| 4,804,750 | 2/1989 | Nishimura et al. | 536/20 |
| 4,921,949 | 5/1990 | Lang et al. | 536/20 |
| 4,971,956 | 11/1990 | Suzuki et al. | 514/55 |
| 5,057,542 | 10/1991 | Leuba et al. | 514/844 |
| 5,262,310 | 11/1993 | Karube et al. | 435/85 |
| 5,567,325 | 10/1996 | Townsley et al. | 210/612 |

OTHER PUBLICATIONS

Segal et al., "Inhibition of Adherence of Candida Albicans to Acrylic by a Chitin Derivative" *European Journal of Epidemiology,* vol. 8(3): 350–355, May 1992.

Okamoto et al., "Dramatic Effect of Chitosan on Infection" *Chitin World,* vol. 6: 395–401, 1994.

Ramisz et al., "The Influence of Chitosan on Health and Production in Pigs" *Chitin World,* vol. 6: 612–616, 1994.

Ghaouth et al., *Physiol. and Molec. Plant Pathol.,* vol. 44: 417–432, (1994).

*Primary Examiner*—Howard C. Lee
*Attorney, Agent, or Firm*—Gifford, Krass, Groh, Sprinkle, Anderson & Citkowski, P.C.

[57] ABSTRACT

An oligomer comprised of repeat units of beta glucosamine exhibits broad antifungal activity. The oligomer preferably has a molecular weight in the range of 4,000–18,000 dalton, and may be partially acetylated. These materials are highly effective against a variety of fungi including various species of Candida.

10 Claims, 2 Drawing Sheets

COMPOSITION AND METHOD FOR TREATING FUNGAL DISEASE IN ANIMALS

FIELD OF THE INVENTION

This invention relates generally to materials and methods for treating fungal disease. More specifically the invention relates to a carbohydrate derived material having utility in treatment of fungal diseases in animals.

BACKGROUND OF THE INVENTION

Fungal infections are common to a large number of animal species. Common agents of fungal infections include various species of the genii Candida and Aspergillus, and types thereof, as well as others. While external fungus infections can be relatively minor, systemic fungal infections can give rise to serious medical consequences. The incidence of fungal infections has undergone a significant increase, particularly in humans. This increase is, at least in part, attributable to an ever increasing number of patients having impaired immune systems, both as a result of medical therapy for other conditions, and as a result of diseases such as AIDS which compromise the immune system. Fungal disease, particularly when systemic, can be life threatening to patients having an impaired immune system.

A number of prior art pharmaceutical agents have been developed for the treatment of fungal diseases. These materials include compounds such as amphotericin B (AMB), triazoles and flucytosin. AMB is the drug of choice for many systemic fungal infections due to its broad range of activity; however, it is harmful to the kidneys and must be administered intravenously. Many of the triazoles exhibit broad ranging activity and can be administered orally; however, many strains of fungi have become resistant to these materials. Consequently, there is a need for a new group of agents which are effective in eliminating fungus disease, but are of low toxicity to patients. Ideally, these materials should be simple to prepare, stable, and easy to administer.

As will be described in further detail hereinbelow, the present invention is directed to a highly effective agent for controlling fungus disease. The material of the present invention is derived from natural carbohydrate materials and is inherently low in toxicity. The material is specifically prepared from complex carbohydrates such as chitin or chitosan. These materials are widely distributed in nature, and are found, for example, in the shells of arthropods, and in the cell walls of fungi. These and other advantages of the present invention will be readily apparent from the discussion, description and examples which follow.

BRIEF DESCRIPTION OF THE INVENTION

There is disclosed herein a therapeutic material for treating fungal diseases in animals. The therapeutic material contains oligomers comprised of repeating units of beta glucosamine. The oligomers have a molecular weight in the range of 4,000 to 18,000 daltons, and in some preferred embodiments fall within the molecular weight range of 4,000 to 7,000 daltons. One specific material of the present invention has a molecular weight range of approximately 4,000 to 5,000 daltons, with the most preferred molecular weight being approximately 4,800 daltons. The beta glucosamine oligomers may be partially acetylated through the nitrogen thereof, and in one specific embodiment the material is approximately 5% to 30% acetylated. Oligomers may, in some instances, be formed by linking the glucosamine units through the four positions thereof.

The material of the present invention may be readily prepared by hydrolysis of chitin, chitosan and similar materials. The hydrolysis may be carried out by treatment with mineral acids or by treatment with enzymes such as cellulase.

Also within the scope of the present invention is a therapeutic method which involves exposing the tissue of an infected animal to the therapeutic agent.

DETAILED DESCRIPTION OF THE INVENTION

Figure 1:
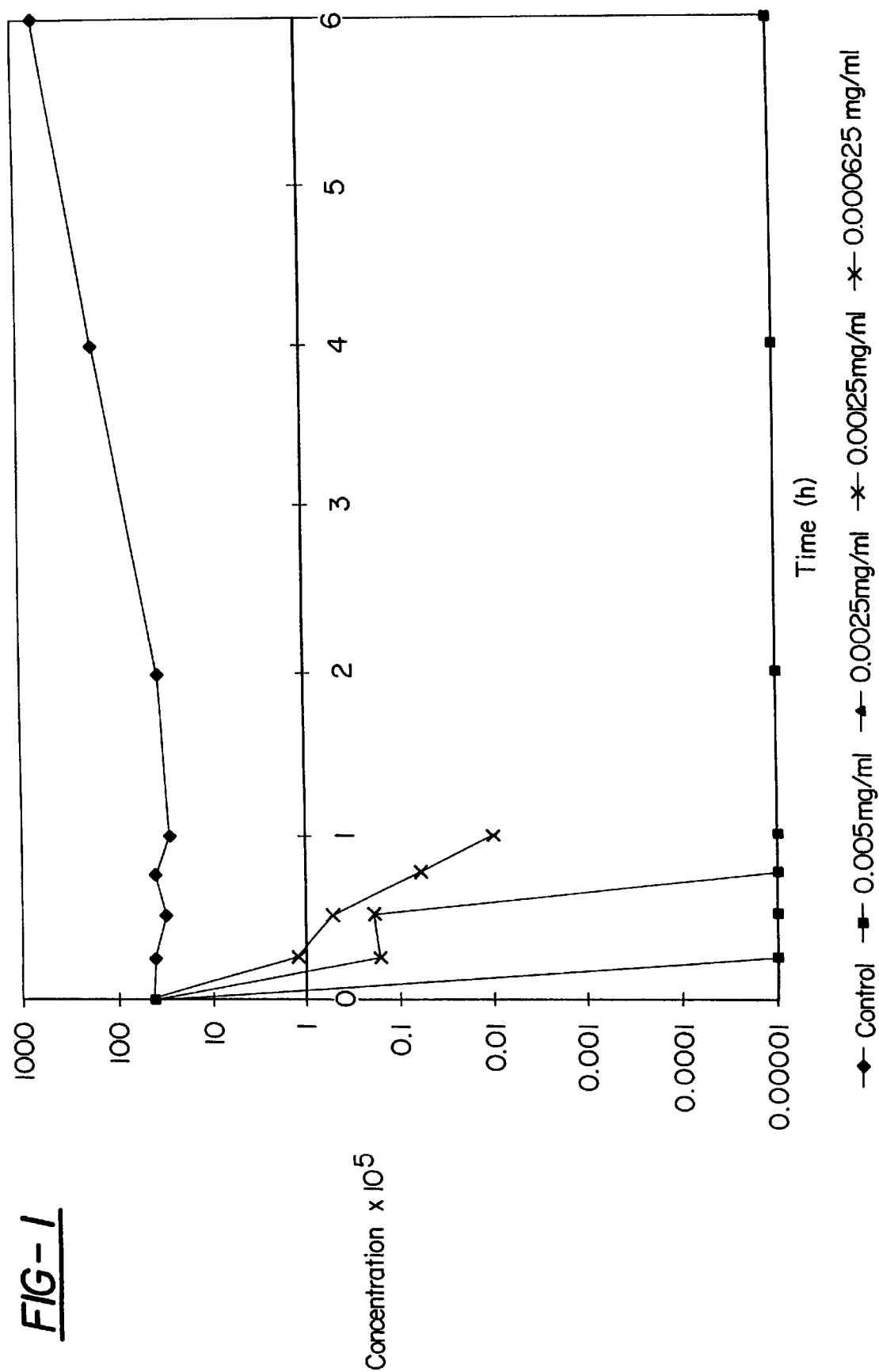
FIG. 1 is a typical kill curve for varying concentrations of the material of the present invention, illustrating its effect against representative isolates of Candida.

In accord with the present invention, it has been found that particular oligomeric materials comprised of linked repeat units of beta glucosamine, and having a molecular weight in the range of 4,000 to 18,000 daltons, are highly effective in killing and/or restricting the growth of a variety of fungal organisms of the type which cause disease in animals, including humans. Within the context of the present invention, fungal organisms are meant specifically to include yeasts. The material of the present invention is most preferably prepared by the hydrolysis of chitin or chitosan. Chitin is a complex polysaccharide and is found in the exoskeletons of arthropods, and in the cell walls of a number of fungi. Chitosan is a semi-synthetic material formed by the at least partial deacetylation of chitin. As will be described in greater detail hereinbelow, the therapeutic material of the present invention is primarily comprised of repeating units of beta glucosamine, and the beta glucosamine units are primarily joined together through their four positions. The basic structure of beta glucosamine is as represented by Formula 1 hereinbelow.

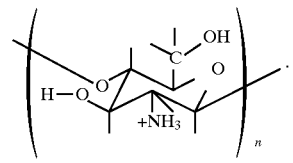

As will be noted, the beta glucosamine is acetylated through the nitrogen thereof, and in the present invention, the preferred therapeutic material has been found to be approximately 5% to 30% acetylated, with the rest comprising the amine. One particular, preferred material is 5% acetylated. In general, materials having a molecular weight in the range of 4,000 to 18,000 daltons have been found to have utility, and materials with a molecular weight in the range of 4,000 to 7,000 daltons have particular utility against a variety of fungi. Most specifically, materials having a molecular weight in the range of 4,000 to 5,000 daltons, and specifically 4,800 daltons, have been shown to manifest particularly high activity against fungi. In general, oligomers of at least 10 repeat units of the beta glucosamine, and more preferably 22 to 25 units, have high demonstrated utility.

The materials of the present invention may be prepared by a variety of methods, including direct synthesis. However, it has been found most economical to prepare the materials by the hydrolysis of chitin or chitosan, since these materials are readily available in large quantities, and at relatively low costs. The hydrolysis may be carried out by the use of mineral acids such as hydrochloric acid, or may be implemented by use of enzymes such as cellulase. In any event, the hydrolysis involves cleavage of an ether linkage joining beta glucosamine units together. Depending upon the strength and time of reaction conditions, the molecular weight of the resultant oligomers may be readily controlled.

Oligomers, in accord with the present invention, were prepared from chitin according to the following procedure. Milled chitin (20 grams), obtained from shrimp shells, and provided by the Sigma Chemical Corporation, was stirred with 300 milliliters of concentrated hydrochloric acid for approximately three hours at 0° C. The resultant suspension of chitin was then hydrolyzed by heating the mixture to 32° C. for approximately one hour. The acidic mixture was adjusted to a pH of approximately 4.0 by the addition of potassium hydroxide. The mixture was centrifuged and the pellet discarded. The supernatant solution was passed through a membrane having a molecular weight cutoff of 20,000. The filtrate was concentrated, then desalted by utilizing a membrane having a cutoff of approximately 400 to 700 molecular weight. This resulted in a mixture of oligo saccharides, which was separated on a Bio-Gel P-4 column, and the different peaks were examined by HPLC. It was found that the material included oligomers having a degree of polymerization of approximately 25, which corresponds to a molecular weight of approximately 5,000.

It has been found that a similar material may be prepared by utilizing chitosan as a starting material. Also, other acids such as trifluoroacetic acid may be similarly employed to effect the hydrolysis.

The oligomers of the present invention may be similarly prepared by enzymatic hydrolysis. In one particular preparation, 9 grams of chitosan, having a molecular weight of approximately 400,000 daltons (obtained from the Sigma Chemical Company) was suspended in 100 milliliters of water. 100 milliliters of 0.5N hydrochloric acid was added to solubilize the chitosan, and the pH adjusted to 5.0 by titration with 0.5N sodium hydroxide. The chitosan solution was diluted to approximately 3%, and 0.5% cellulase enzyme (supplied by the Novo Chemical Company under the name Celluclast, and having up to four units avicelase activity per gram of chitosan) was added. The mixture was heated to 50° C. for six hours. The reaction was then quenched by passing the mixture through a membrane having a molecular weight cutoff of 10,000 daltons. This removed the cellulase and any high molecular weight oligomers. Alternatively, the reaction could be quenched by heating to 85° C. for ten minutes, which deactivates the enzyme. As in the previous example, the resultant oligomer solution was purified by centrifuging and desalting. The product thus produced had a molecular weight in the range of 4,000 to 10,000 daltons. It is to be understood that the reaction conditions employed for the preparation of the oligomers may be readily varied by one of skill in the art, and the present invention is not limited to materials produced by any one specific method, but is directed to the oligomeric material and its utility in the treatment of fungal disease.

Materials thus prepared were analyzed and characterized, through gas chromatography/mass spectrometry, and nuclear magnetic resonance analysis. The analysis confirmed that the main linkage in the oligomers is a four-linked N-acetyl beta glucosamine. The oligomers also include small amounts of 3,4 and 4,6 linked N-acetyl beta glucosamines, and these linkages may represent branching in the oligomers. Both one-dimensional and two-dimensional NMR analyses are consistent with structure being comprised of repeating beta glucosamine units. Molecular weight analysis of the samples was conducted by viscosity measurement as well as size exclusion chromatography, and both were consistent in their determinations.

Experimental Evaluation

The oligomeric material of the present invention was evaluated against various fungi, including strains which are resistant to conventional fungicidal materials. Specifically, the material was evaluated against 99 strains of yeast representing 14 different species. Most of the strains were clinical isolates and the rest were obtained from the American Type and Culture Collection in Rockville, Md. The distribution of species included 29 *Candida albicans* (14 of which are azole resistant); 15 *C. glabrata* (5 of which were azole resistant); 6 *C. parapsilosis* (1 of which was azole resistant); 6 *C. lusitaniac*; 2 *C. rugosa*; 10 *C. tropicalis* (2 of which were azole resistant); 1 azole resistant *C. lambica*; 8 azole resistant *C. crusei*; 9 *C. guillermondii*; 5 *C. kefyr*; 4 *C. stalatoidea*; 1 *C. paratropicalis*; 1 *C. lipolitica*; and 2 *Saccharomyces cerevisiae*. The material was also evaluated against 20 species of Aspergillus fumigatus. Ten of these strains represented clinical isolates from the microbiology laboratory of the Detroit Medical Center; 5 were laboratory isolates each resistant to itraconazole and amphotericin B.

Working cultures of the foregoing were prepared using conidia as inoculum on YPD agar slants obtained from the Sigma Chemical Company of St. Louis, Mo. The slants were incubated at 30° C. for four days or until the cultures conidiate and fresh conidia from the subcultures were used as a source of inoculum for all of the cultures in the subsequent work.

The material employed in this evaluation was an oligomeric material comprised of repeat units of beta glucosamine, having a molecular weight of approximately 4,800 dalton. The material was prepared by the acid hydrolysis of chitosan in accord with the aforedescribed procedures. The particular material employed was designated CAN-296 and was utilized as a 0.1 mg/ml aqueous solution in the yeast antifungal susceptibility assays.

The minimum inhibitory concentration (MIC) and minimum lethal concentration (MLC) of the CAN-296 material was determined by using both the broth microdilution method as recommended by the National Committee for Clinical Laboratory Standards (NCCLS document M27; 1992), except that TYG was used as an assay medium instead of RPMI 1640. In accord with the procedure, the microorganisms were grown in PYG medium to which the CAN-296 material was added in concentrations ranging from 10 to 0.019 micrograms per milliliter. The MIC was defined as the lowest concentration that inhibited growth completely. MICs were measured after 48 hours of incubation at 35° C. MLC was determined by subculturing 100 microliters from the first concentration demonstrating complete growth inhibition and from all concentrations that had no visible growth. The subculturing was done on Sabouraud dextrose agar plates that were incubated at 30° C. for 24 hours (72 hours for Cryptococcus species). MLC was defined as the lowest concentration at which 99% of the initial inoculum was killed.

Aspergillus Fumigatus Susceptibility Studies

The susceptibility of A. fumigatus to CAN-296 as well as to itraconazole and amphotericin B was determined by the broth macrodilution technique according to the procedure of Espinel-Ingroff et al. as modified by Manavathu et al. using fresh conidia as the source of inoculum. For the preparation of conidial suspensions, cultures of various isolates were grown on yeast extract peptone dextrose (YPD) agar plates obtained from the Sigma Chemical Company, for six days at 30° C. until the whole plate was covered with fungal growth. The conidia were collected by flooding the agar surfaces with sterile growth medium (approximately 22 milliliters) followed by gentle scraping with a sterile rubber policeman. The resulting suspension containing fragments of mycelia, small pieces of agar and other cellular debris was collected by aspiration. The aspirate was vortexed vigorously to release conidia from the conidiophores and was filtered through a sterile cotton plug fitted into a sterile filtration funnel. The cell density was determined by hemocytometer count. Each sample was counted four times independently, and the mean value of the quadruplicate was used for the calculation of the cell density. Typically, $1-3 \times 10^7$ conidia per milliliter were obtained when 20 milliliters of growth medium was used for resuspension. The relationship between cell density, as estimated by hemocytometer count, and the number of colony forming units was determined by plating appropriately diluted cell suspensions onto YPD agar. The cell density estimation by colony forming units (CFU) production was approximately 10–20% lower than the value obtained by hemocytometer count.

The broth macrodilution experiments were performed in sterile 6 milliliter polystyrene tubes with a final volume of 1 milliliter. Two times the required final concentration of CAN-296, itraconazole and AMB were prepared in 0.5 ml growth medium by two-fold serial dilutions. Each sample container was inoculated with 0.5 ml of conidial suspension (two times the required final CFU prepared in growth medium by two-fold serial dilution) to obtain a final CFU of $1 \times 10^4$ per ml. Each series of drug concentration was tested in triplicate and each MIC determination was repeated at least once. The AMB tubes were wrapped in aluminum foil to prevent light exposure, and all tubes were incubated at 35° C. for 48 hours, and, after vortexing, with scraping of the walls if necessary, were scored for visible growth. The MIC was defined as the lowest concentration of drug in which no visible growth occurred.

Time Kill Study

The fungicidal activity of CAN-296 was examined by kill curve experiments using two C. albicans isolates (B311 and 90028) and C. glabrata (32554). In this study, test organisms were grown in YPD broth for 24 hours at 30° C. on a gyratory shaker at 160 rpm. The culture was diluted approximately 1,000-fold to obtain a cell density of $1 \times 10^6$ forming units (CFU) per ml. Five ml aliquots of the diluted cultures were incubated at 30° C. with various concentrations of CAN-296 ranging from 0 to 5 micrograms per ml. At various time intervals of 0–24 hours, 0.1 ml aliquots of cell suspension were removed, serially diluted ($10^2$ to $10^6$ fold) and 0.1 ml aliquots were spread on YPD agar plates in replicates. After incubation at 30° C. for 48 hours, the number of CFU per ml of cultures were estimated and plotted against the time of exposure to the CAN-296 so as to construct a kill curve.

Results

Table 1 summarizes the results testing the effectiveness of the CAN-296 compound of the present invention against a variety of yeasts. The table represents MIC data for the subject material as well as for preventional fungicides including AMB, flucytosine, ketoconazole, fluconazole, itraconazole, and the pneumocandin L-733,560. The table also presents MLC data for the CAN-296 material. As will be seen, the vast majority of the tested species show a highly uniform susceptibility to CAN-296 at concentrations of 0.078 to 0.312 micrograms per ml. Azole-resistant and azole-susceptible Candida species were similarly sensitive, and when compared to L-733,560, CAN-296 has a narrower and more consistent therapeutic range. The MICs of CAN-296 are comparable with those of AMB. Only one strain of C. glabrata was shown to be resistant to CAN-296 at 10 micrograms per ml. For all azole susceptible and resistant Candida species, the MIC and MLC did not differ by more than two-fold. The fungicidal action was fast; it was observed within 15 minutes at a concentration of 2.5 to 5 micrograms per ml, within 45 minutes at a concentration of 1.25 micrograms per ml, and within 120 minutes at a concentration of 0.625 micrograms per ml. FIG. 1 depicts typical kill curves for the different Candida isolates. The concentrations of CAN-296 used for the time-kill study ranged from approximately 2–16 fold, the main MIC value for most Candida species. As shown in FIG. 1, the fungicidal activity of CAN-296 was both concentration and time dependent. Greater than 99.999% of the cells were killed within 15 minutes of exposure to the compound when the CAN-296 concentration used was greater than eight-fold the MIC.

TABLE 1

| Organism | Antifungal Agent | MIC µg/ml Range | MLC µg/ml Range |
| --- | --- | --- | --- |
| C. albicans (29) | CAN-296 | 0.156–0.312 | 0.156–0.312 |
|  | Amphotericin B | 0.02–0.1 |  |
|  | Flucytosine | 0.04–1.25 |  |
|  | Ketoconazole | 0.01–6.25 |  |
|  | Fluconazole | 0.08–>80 |  |
|  | Itraconazole | 0.01–12.5 |  |
|  | L-733, 560 | 0.05–0.78 |  |
| C. parapsilosis (6) | CAN-296 | 0.078–0.312 | 0.078–0.312 |
|  | Amphotericin B | 0.05–0.2 |  |
|  | Flucytosine | 0.08–1.25 |  |
|  | Ketoconazole | 0.02–0.2 |  |
|  | Fluconazole | 0.16–>20 |  |
|  | Itraconazole | 0.02–0.2 |  |
|  | L-733, 560 | 0.02–1.56 |  |
| C. glabrata (15) | CAN-296 | 0.078–0.312 | 0.078–0.312 |
|  | Amphotericin B | 0.05–0.2 |  |
|  | Flucytosine | 0.04–0.3 |  |
|  | Ketoconazole | 0.01–6.3 |  |
|  | Fluconazole | 1.25–>40 |  |
|  | Itraconazole | 0.02–6.3 |  |
|  | L-733, 560 | 0.1–0.39 |  |
| C. tropicalis (10) | CAN-296 | 0.039–0.312 | 0.039–0.312 |
|  | Amphotericin B | 0.02–0.39 |  |
|  | Flucytosine | 0.08–0.63 |  |
|  | Ketoconazole | 0.02–3.12 |  |
|  | Fluconazole | 0.63–>80 |  |
|  | Itraconazole | 0.02–6.25 |  |
|  | L-733, 560 | 0.1–0.78 |  |
| C. lusitaniae (6) | CAN-296 | 0.156–0.312 | 0.156–0.312 |
|  | Amphotericin B | 0.05 |  |
|  | Flucytosine | 0.08 |  |
|  | Ketoconazole | 0.02–0.2 |  |
|  | Fluconazole | 0.31–>20 |  |
|  | Itraconazole | 0.02–0.1 |  |
|  | L-733, 560 | 0.39–0.78 |  |
| C. krusei (8) | CAN-296 | 0.039–0.312 | 0.039–0.312 |
|  | Amphotericin B | 0.1–0.39 |  |
|  | Flucytosine | 2.5–20 |  |
|  | Ketoconazole | 0.01–1.56 |  |
|  | Fluconazole | 10–>80 |  |

TABLE 1-continued

| Organism | Antifungal Agent | MIC µg/ml Range | MLC µg/ml Range |
|---|---|---|---|
| | Itraconazole | 0.01–0.39 | |
| | L-733, 560 | 0.78 | |
| C. guillermondii (9) | CAN-296 | 0.078–0.312 | 0.078–0.312 |
| | Amphotericin B | 0.2–0.78 | |
| | Flucytosine | 0.08–0.16 | |
| | Ketoconazole | 0.02–0.1 | |
| | Fluconazole | 5–>10 | |
| | Itraconazole | 0.02–0.78 | |
| | L-733, 560 | 0.78–1.56 | |
| C. kefyr (5) | CAN-296 | 0.156–0.312 | 0.156–0.312 |
| | Amphotericin B | 0.05–0.39 | |
| | Flucytosine | 0.08–0.16 | |
| | Ketoconazole | 0.02 | |
| | Fluconazole | 0.31–2.5 | |
| | Itraconazole | 0.2 | |
| | L-733, 560 | 0.02–0.78 | |
| C. stellatoidea (4) | CAN-296 | 0.312 | 0.312 |
| | Flucytosine | 0.625–1.25 | |
| | Ketoconazole | 0.01 | |
| | Fluconazole | 0.16–0.31 | |
| | Itraconazole | 0.01 | |
| C. rugosa (2) | CAN-296 | 0.312 | 0.312 |
| | Flucytosine | 0.08 | |
| | Ketoconazole | 0.01 | |
| | Fluconazole | 5 | |
| | Itraconazole | 0.02 | |
| C. lambia (1) | CAN-296 | 0.078 | 0.078 |
| | Amphotericin B | 0.01 | |
| | Flucytosine | 0.31 | |
| | Ketoconazole | 0.01 | |
| | Fluconazole | 20 | |
| | Itraconazole | 0.01 | |
| C. paratropicalis (1) | CAN-296 | 0.312 | 0.312 |
| C. lipolitica (1) | CAN-296 | 0.312 | 0.312 |
| Saccharomyces C. (2) | CAN-296 | 0.156 | 0.156 |

Figure 2:
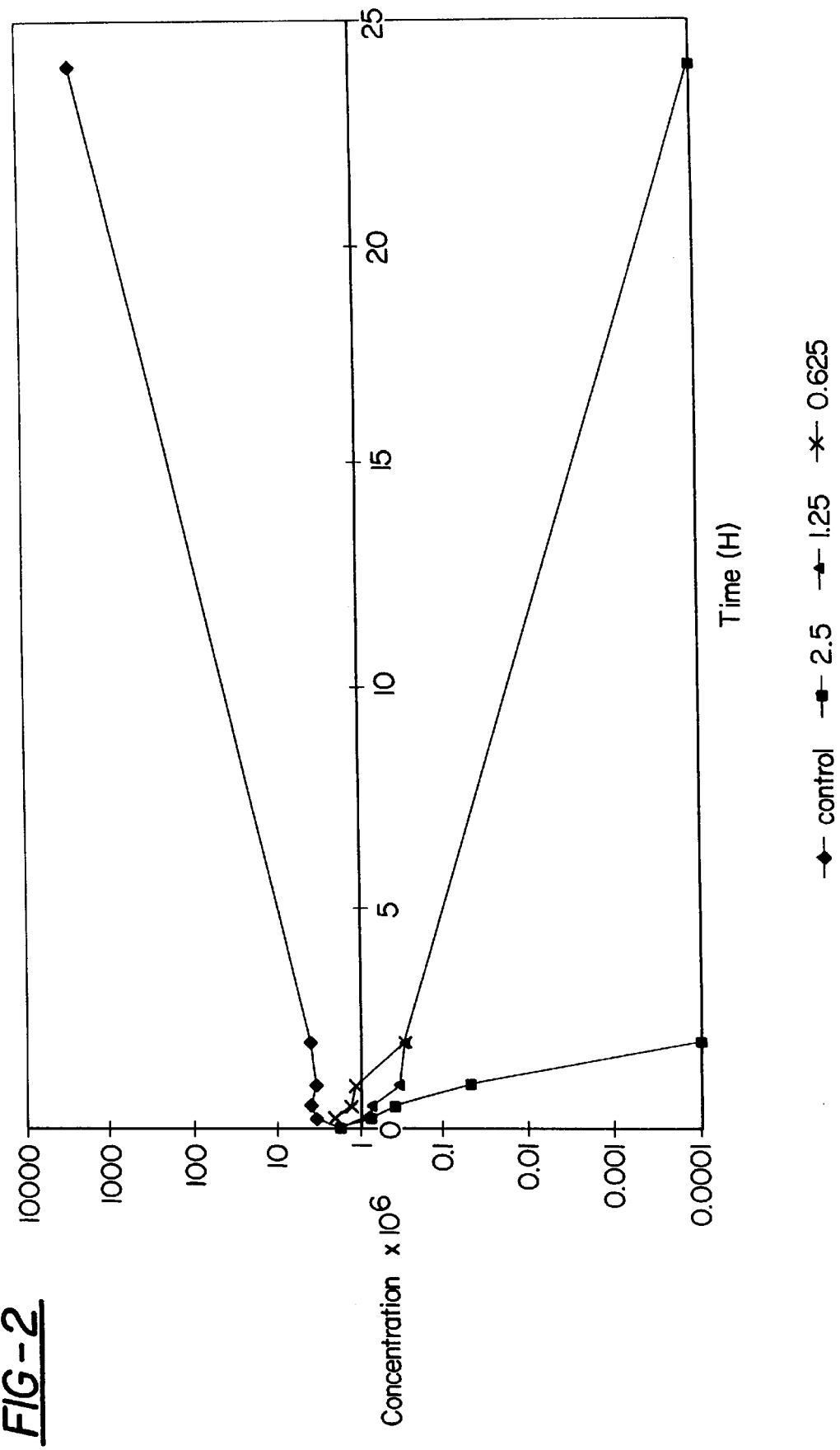
FIG. 2 is a kill curve showing the effect of various concentrations of the material of the present invention as applied to a specific strain of Candida albicans90028.

Referring now to FIG. 2, there is shown the kill curve for the CAN-296 material as was developed with regard to the C. albicans strain 90028.

Table 2 summarizes a comparison of the MIC values of CAN-296 for a variety of strains of A. fumigatus, as compared to itraconazole and AMB. It will be noted that the CAN-296 material is somewhat less effective against aspergillus than it is against yeasts; however, it is notable that both the itraconazole resistant and AMB resistant strains of aspergillus do not demonstrate any resistance to the material of the present invention.

TABLE 2

| | MIC (µg/ml) | | |
|---|---|---|---|
| Microorganism | CAN296 | ITZ | AMB |
| Aspergillus fumigatus W73355 | 0.625 | 0.25 | 0.5 |
| Aspergillus fumigatus W27023 | >5 | 0.25 | 0.5 |
| Aspergillus fumigatus W37825 | >5 | 0.25 | 0.5 |
| Aspergillus fumigatus W60252 | >5 | 0.25 | 0.5 |
| Aspergillus fumigatus M38358 | >5 | 0.25 | 0.5 |
| Aspergillus fumigatus X8069 | >5 | 0.25 | 0.5 |
| Aspergillus fumigatus H33233 | >5 | 0.25 | 0.5 |
| Aspergillus fumigatus H52950 | >5 | 0.25 | 1 |
| Aspergillus fumigatus H38375 | >5 | 0.25 | 0.5 |
| Aspergillus fumigatus W45777 | >5 | 0.25 | 0.25 |
| Aspergillus fumigatus AB8.36 | >5 | 0.25 | 4 |
| Aspergillus fumigatus AB8.56 | >5 | 0.25 | 4 |
| Aspergillus fumigatus AB8.95 | >5 | 0.5 | 4 |
| Aspergillus fumigatus AB16.2 | >5 | 0.125 | 2 |
| Aspergillus fumigatus AB16.3 | >5 | 0.25 | 4 |
| Aspergillus fumigatus ITZ5 | 5 | >16 | 0.5 |
| Aspergillus fumigatus ITZ25 | >5 | >16 | 1 |
| Aspergillus fumigatus ITZ40 | >5 | >16 | 0.5 |
| Aspergillus fumigatus ITZ51 | >5 | >16 | 1 |
| Aspergillus fumigatus ITZ70 | 5 | >16 | 0.5 |

The heat and pH stability of CAN-296 was evaluated, and it was found that boiling for 60 minutes failed to affect its ability to inhibit the growth of C. albicans B311 and p0028, indicating that it is a heat stable compound. The material was also found to be pH stable and no differences in MIC results were noted when the pH of the medium (PYG) was varied.

The foregoing study demonstrates that the material of the present invention is a highly effective, broad spectrum antifungal agent. It is effective, even against species and strains which are resistant to conventional antifungal materials. Furthermore, it appears that no cross resistance occurs between the material of the present invention and conventionally employed antifungal agents. The material of the present invention produces a very rapid killing of fungus, typically within 15 minutes of exposure, thereby suggesting that this mode of action is unique. While not wishing to be bound by speculation, it is believed to be possible that the material of the present invention may poison an enzymatic system of the fungus or otherwise interfere with cell metabolism. The demonstrated heat and pH stability of the material increases its utility by permitting a variety of delivery systems to be used and further simplifying storage and handling. Since the material is not degraded by gastric acids, it may be administered in an oral form; although in some instances, it may be advantageously administered intravenously.

While experimental data regarding one specific material has been presented, it will be understood from the foregoing that various molecular weight fractions, as well as mixtures of oligomers may be employed in the practice of the present invention. The foregoing figures, data, examples and discussion are merely meant to illustrate particular embodiments of the invention and are not meant to be limitations upon the practice thereof. It is the following claims, including all equivalents, which define the scope of the invention.

I claim:

1. A method of treating fungal disease in animals comprising:
    exposing the tissue of said animal to a therapeutic agent comprising: oligomers comprised of linked repeat units of beta glucosamine, said oligomers having a molecular weight in the range of 4,000 to 18,000 daltons.

2. A method as in claim 1, wherein said oligomers have a molecular weight in the range of 4,000 to 7,000 daltons.

3. A method as in claim 1, wherein said oligomers have a molecular weight in the range of 4,000 to 5,000 daltons.

4. A method as in claim 1, wherein said oligomers have a molecular weight of approximately 4,800 daltons.

5. A method as in claim 1, wherein at least a portion of the beta glucosamine repeat units are acetylated through the nitrogen thereof.

6. A method as in claim 5, wherein approximately 5% to 30% of the beta glucosamine repeat units are acetylated.

7. A method as in claim 1, wherein the repeat units of beta glucosamine comprising said oligomers are joined through 1-4 A linkages thereof.

8. A method as in claim 1, wherein oligomers are comprised of at least ten linked repeat units of beta glucosamine.

9. A method as in claim 8, wherein said oligomers comprise approximately 22 to 25 of said repeat units.

10. A method of treating fungal disease in animals, caused by infection with Candida or Aspergillus; said method comprising exposing the tissue of said animal to a therapeutic agent comprising oligomers comprised of linked repeat units of beta glucosamine, said oligomers having a molecular weight in the range of 4,000 to 18,000 daltons.

* * * * *